US008342170B2

(12) United States Patent
Kitakami

(10) Patent No.: US 8,342,170 B2
(45) Date of Patent: Jan. 1, 2013

(54) LIQUID EJECTION METHOD AND LIQUID EJECTION APPARATUS

(75) Inventor: Koichi Kitakami, Chigasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 749 days.

(21) Appl. No.: 12/467,606

(22) Filed: May 18, 2009

(65) Prior Publication Data

US 2009/0293871 A1 Dec. 3, 2009

(30) Foreign Application Priority Data

May 30, 2008 (JP) ................................. 2008-142678

(51) Int. Cl.
*A61M 15/00* (2006.01)

(52) U.S. Cl. .......... 128/200.14; 128/200.21; 128/203.16

(58) Field of Classification Search ........... 128/200.14–200.24, 203.15–203.16
See application file for complete search history.

(56) References Cited

U.S. PATENT DOCUMENTS

| | | | | |
|---|---|---|---|---|
| 6,601,945 | B2 | 8/2003 | Kitakami | 347/40 |
| 6,769,626 | B1 * | 8/2004 | Haveri | 239/102.2 |
| 6,926,392 | B2 | 8/2005 | Sasaki et al. | |
| 7,419,235 | B2 | 9/2008 | Kitakami | 347/14 |
| 7,766,253 | B2 * | 8/2010 | Le Pesant et al. | 239/102.1 |
| 2008/0029084 | A1 * | 2/2008 | Costantino et al. | 128/200.14 |
| 2008/0216824 | A1 * | 9/2008 | Ooida | 128/200.21 |
| 2008/0223953 | A1 * | 9/2008 | Tomono et al. | 239/102.2 |
| 2008/0291236 | A1 | 11/2008 | Kitakami et al. | 347/30 |

FOREIGN PATENT DOCUMENTS

| | | |
|---|---|---|
| JP | 2003-154665 | 5/2003 |
| JP | 2005-231086 | 9/2005 |

* cited by examiner

*Primary Examiner* — Lynne Anderson
(74) *Attorney, Agent, or Firm* — Fitzpatrick, Cella, Harper & Scinto

(57) ABSTRACT

The present invention provides a liquid ejection method and a liquid ejection apparatus which enables small droplets each of diameter at most 10 μm to be stably ejected and which allows a sufficient number of droplets to be ejected per unit time. A heater is allowed to generate heat to eject a main droplet and a liquid column from an ejection port; the liquid column is to be separated into a plurality of sub-droplets. A relationship $(L2/L1) \geqq 0.9$ is set for the length L1 of the liquid column observed immediately after the liquid column has been separated from the main droplet and from a liquid in the ejection port and the length L2 of the liquid column observed immediately before the liquid column is separated into the plurality of droplets.

5 Claims, 8 Drawing Sheets

LIQUID EJECTION METHOD AND LIQUID EJECTION APPARATUS

BACKGROUND OF THE INVENTION

1. Field of the Invention

The present invention relates to a liquid ejection method and a liquid ejection apparatus which eject a fine droplet of liquid, and in particular, to a liquid ejection method and a liquid ejection apparatus which are suitably used in the medical field to allow a liquid drug to be sucked into the lungs in the form of a liquid mist.

2. Description of the Related Art

Keen examinations have been made of applications of liquid ejection apparatuses ejecting fine a droplet of liquid, in the fields of ink jet printing and medical care (particularly, the field of drug suction). Various such apparatuses have been proposed.

For example, Japanese Patent Laid-Open No. 2003-154665 discloses a liquid ejection head in which individual liquid chambers and ejection ports through which ink is ejected are coupled together via throttling portions of pore diameter 3 μm to allow a droplet of diameter 3 μm (volume: 0.014 picolitters) to be ejected.

In general, the size of the ejection port (in the example in Japanese Patent Laid-Open No. 2003-154665, the throttling portion pore) is reduced to allow a smaller droplet to be ejected. However, when the size of the ejection port, that is, the diameter thereof, is smaller than 10 μm, the liquid in the ejection port changes rapidly as a result of drying or the like, hindering the liquid from being properly ejected. Furthermore, if a recovery process is frequently executed to maintain proper liquid ejections, costs are increased, and ink is wastefully discharged. Thus, in the field of ink jet printing, little effort has been made to provide products with the ejection port of diameter at most 5 μm.

According to the technique disclosed in Japanese Patent Laid-Open No. 2003-154665, a relatively large ejection port is provided outside a small throttling portion pore of diameter about 3 μm. Fluctuation of the liquid surface of a meniscus in the liquid formed in the ejection port seriously affects a direction in which a very small droplet of diameter 3 μm (volume: 0.014 picolitters) fly. This also discourages effort to develop products with the ejection port of diameter 3 μm. However, in the field of drug suction, variation in the flying direction of liquid droplet is somewhat allowable.

On the other hand, in the development of a technique for reducing the size of the ejection port (in the example in Japanese Patent Laid-Open No. 2003-154665, the throttling portion pore) and thus the size of the ejected liquid droplet, an increase in the flow resistance of the liquid hinders the droplet from being properly ejected. Thus, in the conventional art, the minimum possible diameter of the throttling portion pore is about 3 μm. A thin throttling portion of thickness 1 μm may be damaged or broken by the flow of the liquid during ejection. Furthermore, if an ejection port of a relatively large diameter is formed outside the throttling portion pore as in the case of Japanese Patent Laid-Open No. 2003-154665, the liquid in the ejection port needs to be raised upon being ejected to the exterior. This hinders the liquid from being properly ejected. Thus, in the conventional art, making the diameter of the throttle portion pore smaller than 3 μm is difficult.

Japanese Patent Laid-Open No. 2005-231086 discloses a liquid ejection head with an ejection port and a throttling portion pore similar to those in Japanese Patent Laid-Open No. 2003-154665. As described in Japanese Patent Laid-Open No. 2005-231086, setting the diameter of the throttling portion pore to about 3 μm increases time required to complete refilling the liquid. Thus, in the conventional art, also in connection with the refilling of the liquid, making the diameter of the throttle portion pore smaller than 3 μm is difficult.

In the field of drug suction, there has been a demand for a liquid ejection apparatus which enables a small droplet of diameter 10 μm (volume: 0.5 picolitters) to be ejected and which allows a sufficient number of liquid droplets to be ejected per unit time without improperly ejecting the liquid as a result of possible drying.

SUMMARY OF THE INVENTION

The present invention provides a liquid ejection method and a liquid ejection apparatus which enables a small droplet of diameter at most 10 μm to be stably ejected and which allows a sufficient number of droplets to be ejected per unit time.

In the first aspect of the present invention, there is provided a liquid ejection method of ejecting a liquid containing a drug to be sucked into lungs using a liquid ejection head in which an individual liquid chamber and an ejection port communicate with each other through a throttling portion having a smaller opening area than the ejection port, the individual liquid chamber being supplied with the liquid, the individual liquid chamber including an energy generation portion generating energy required to eject the liquid, the energy generating section being driven to eject the liquid in the individual liquid chamber from the ejection port through the throttling portion, wherein the energy generation portion is driven to eject a main droplet and a liquid column from the ejection port, the liquid column being to be separated into a plurality of sub-droplets, and a relationship $(L\mathbf{2}/L\mathbf{1}) \geqq 0.9$ is set for length L1 of the liquid column observed immediately after the liquid column has been separated from the main droplet and from the liquid in the ejection port and length L2 of the liquid column observed immediately before the liquid column is separated into the plurality of droplets.

In the second aspect of the present invention, there is provided a liquid ejection apparatus ejecting a liquid containing a drug to be sucked into lungs, the apparatus comprising: a liquid ejection head in which an individual liquid chamber and an ejection port communicate with each other through a throttling portion having a smaller opening area than the ejection port, the individual liquid chamber being supplied with the liquid, the individual liquid chamber including an energy generation portion generating energy required to eject the liquid; and a driving circuit driving the energy generating section to eject the liquid in the individual liquid chamber from the ejection port through the throttling portion, wherein the driving circuit drives the energy generation portion to allow a main droplet and a liquid column to be ejected from the ejection port, the liquid column being to be separated into a plurality of sub-droplets and to set a relationship $(L\mathbf{2}/L\mathbf{1}) \geqq 0.9$ for length L1 of the liquid column observed immediately after the liquid column has been separated from the main droplet and from the liquid in the ejection port and length L2 of the liquid column observed immediately before the liquid column is separated into the plurality of droplets.

In the third aspect of the present invention, there is provided a liquid ejection method of ejecting a liquid containing a drug to be sucked into lungs, the method comprising the steps of: preparing a liquid ejection head having an individual liquid chamber including an energy generation portion generating energy required to eject the liquid, an ejection port formed of a recess portion to internally hold the liquid, and a throttling portion formed to have a smaller opening than the ejection port and allowing the individual liquid chamber and the ejection port to communicate with each other; and driving the energy generation portion so as to eject a main droplet and a liquid column from the ejection port, the liquid column being to be separated into a plurality of sub-droplets, wherein droplets ejected from one ejection port by a single operation of driving the energy generation portion and containing the main droplet and the sub-droplets contains at least five droplets each of diameter at least 1.0 μm and at most 5.0 μm.

The present invention allows the liquid ejection head to eject the liquid so that variation in the length of the liquid column ejected from the ejection port in the liquid ejection head meets a predetermined condition. Thus, the liquid column is separated into a large number of sub-droplets, allowing a sufficient number of droplets to be ejected per unit time. For example, several tens of microlitters of small droplets each of about diameter 3 μm can be stably ejected every second. Such droplet ejections are suitable for allowing, in the field of medical care, a liquid drug to be sucked into the lungs in the form of a liquid mist.

Furthermore, a single operation of driving an energy generation portion generating energy required to eject ink allows a large number of sub-droplets to be formed. Thus, a sufficient number of droplets can be ejected per unit time by driving the energy generation portion only a few times. As a result, energy can be efficiently used to drive the liquid ejection head. This also allows the liquid ejection head to last long. The throttling portion between the ejection port and the individual liquid chamber is positioned in the liquid forming a meniscus in the ejection port. Thus, the liquid in the throttling portion is prevented from being clogged by drying. Therefore, the liquid can be continuously appropriately ejected from the beginning of the liquid ejection.

Further features of the present invention will become apparent from the following description of exemplary embodiments (with reference to the attached drawings).

DESCRIPTION OF THE EMBODIMENTS

Embodiments of the present invention will be described below with reference to the drawings.

First Embodiment

Figure 4:
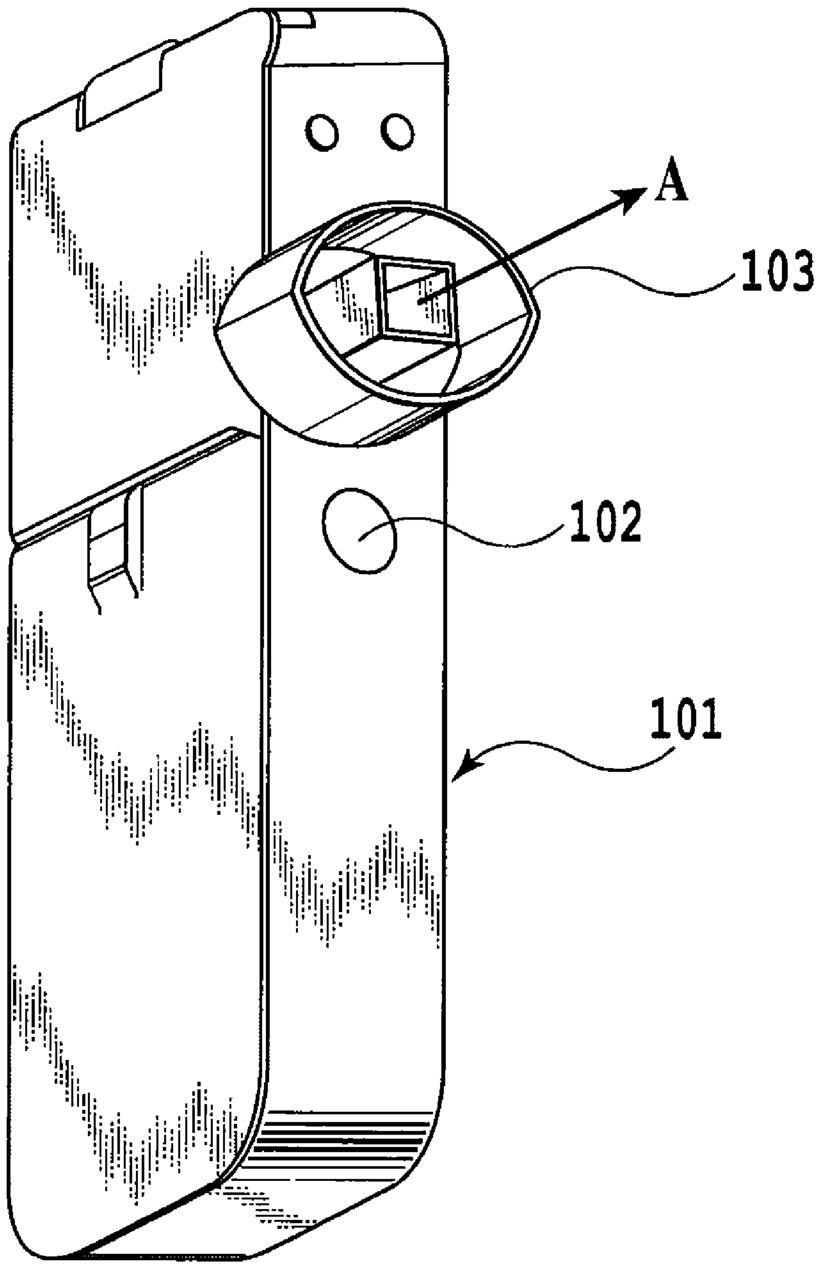
FIG. 4 is a perspective view of a liquid ejection apparatus to which the present invention is applicable.

FIG. 4 is a perspective view of a liquid ejection apparatus to which the present invention is applicable. The liquid ejection apparatus in the present example is a medical suction apparatus used to allow a liquid drug (chemical) to be sucked into the lungs in the form of a liquid mist. A power switch 102 on an apparatus main body 101 is turned on to allow a driving circuit (not shown in the drawing) to drive a liquid ejection head. Then, the chemical stored in the apparatus main body 101 is ejected from the liquid ejection head in the direction of arrow A. The ejected and nebulized chemical is then sucked into the patient's mouth or the like through a mouthpiece 103.

Figure 5:
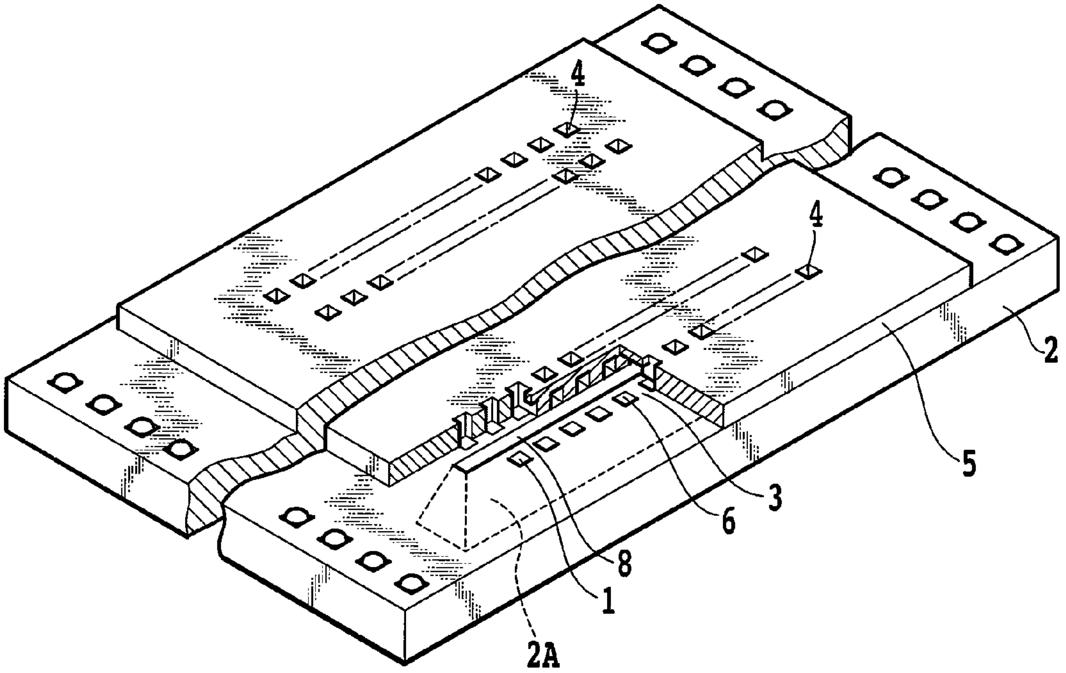
FIG. 5 is a partly cutaway perspective view illustrating an example of the basic configuration of the liquid ejection head.

FIG. 5 is a schematic perspective view illustrating an example of the basic configuration of the liquid ejection head. In the ejection head in the present example, electrothermal converters (heaters) 1 are used as energy generation portions that generate energy required to eject a liquid. That is, the heaters 1, formed on a substrate 2, are located opposite ejection ports 4 formed on a plate 5. The liquid is fed into individual liquid chambers 6 containing the respective heaters 1. Each of the heaters 1 generates heat to bubble the liquid in the corresponding individual liquid chamber 6. The expansion energy of the generated bubble can be utilized to eject the liquid from the corresponding ejection port 4. The liquid is fed through a liquid supply port 2A formed in the substrate 2, to a common liquid chamber 8 formed between the substrate 2 and the plate 5. Moreover, the liquid in the common liquid chamber 8 is fed to each of the individual liquid chambers 6 through the corresponding liquid channel 3, formed between the substrate 2 and the plate 5.

Instead of the heater 1, a piezo element or the like may be used as an energy generation portion. The present embodiment only requires that the liquid fed into the individual liquid chamber 6 can be ejected from the corresponding ejection port 4. The number, shape, arrangement form, and the like of ejection ports 4 formed may be varied depending on the type of the liquid to be ejected and the intended use and are not limited to the configuration shown in FIG. 5.

Figure 1:
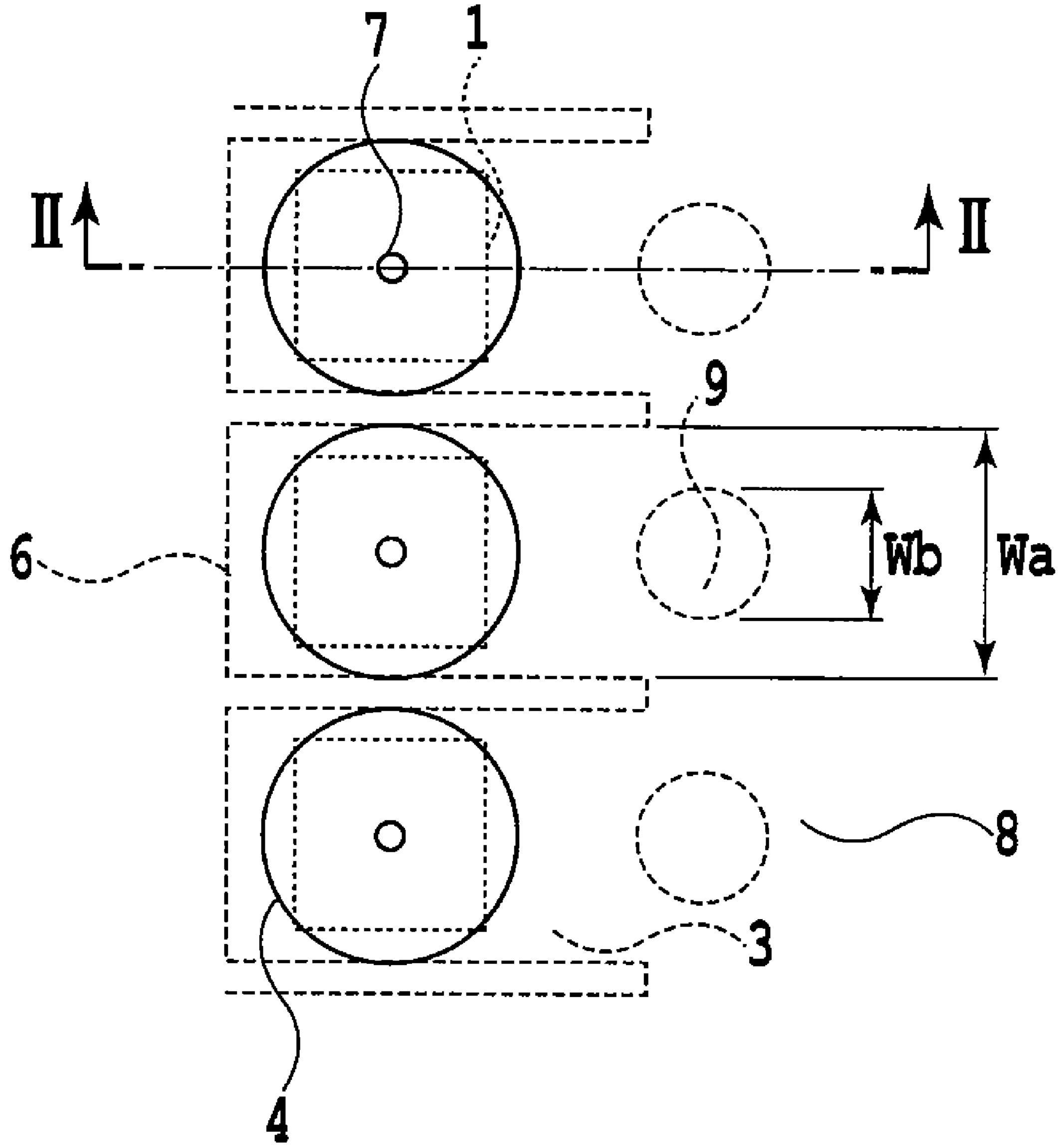
FIG. 1 is a plan view of an essential part of a liquid ejection head used in a first embodiment of the present invention.
Figure 2:
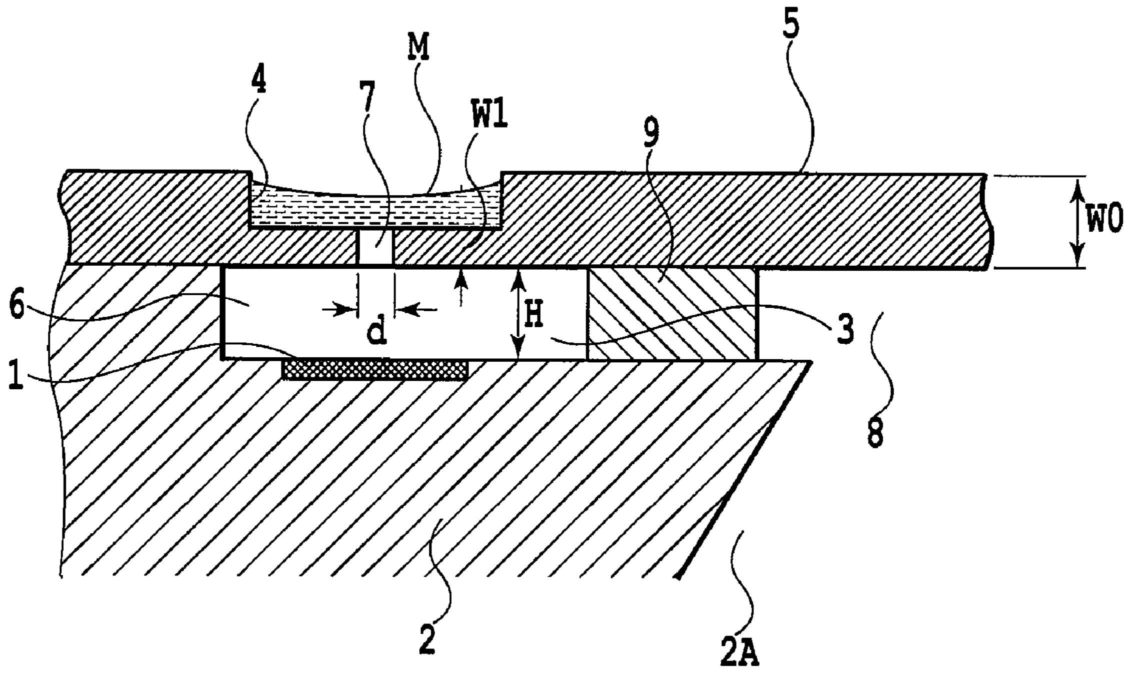
FIG. 2 is a sectional view taken along line II-II in FIG. 1.

FIGS. 1 and 2 are diagrams illustrating the ejection head basically configured as shown in FIG. 5 and applied to the medical suction apparatus in FIG. 4. FIG. 1 is an enlarged plan view of an essential part of the liquid ejection head. FIG. 2 is a sectional view taken along line II-II in FIG. 1.

In the liquid ejection head in the present example, a pore 7 serving as a throttling portion is formed between each of the individual liquid chambers 6 and the corresponding ejection port 4; the pore 7 has a smaller opening area than the ejection port 4. The individual liquid chamber 6 and the ejection port 4 communicate with each other through the pore 7. The individual liquid chamber 6 has a height H of 5 μm, and the plate 5 has a thickness W0 of 5 μm. The pore 7 has a diameter d of 2 μm, and the heater 1 has a square shape 15 μm on a side. In view of the fact that the flow resistance of the chemical increases consistently with the thickness of the plate 5, the plate 5 has a thickness W1 of 2 μm in a part thereof corresponding to the pore 7 in order to offer an appropriate strength and to allow the chemical to flow straight. Reference character M denotes a meniscus of the chemical formed in the ejection port 4. A flow resistance member 9 is provided in the liquid channel 3 between the individual liquid chamber 6 and the common liquid chamber 8 to offer resistance to the flow of the chemical. The flow resistance member 9 in the present example has a cylindrical shape with a diameter Wb (=Wa/2) that covers half of the width Wa of the individual liquid chamber 6.

Figures 3A, 3B, 3C, 3D:
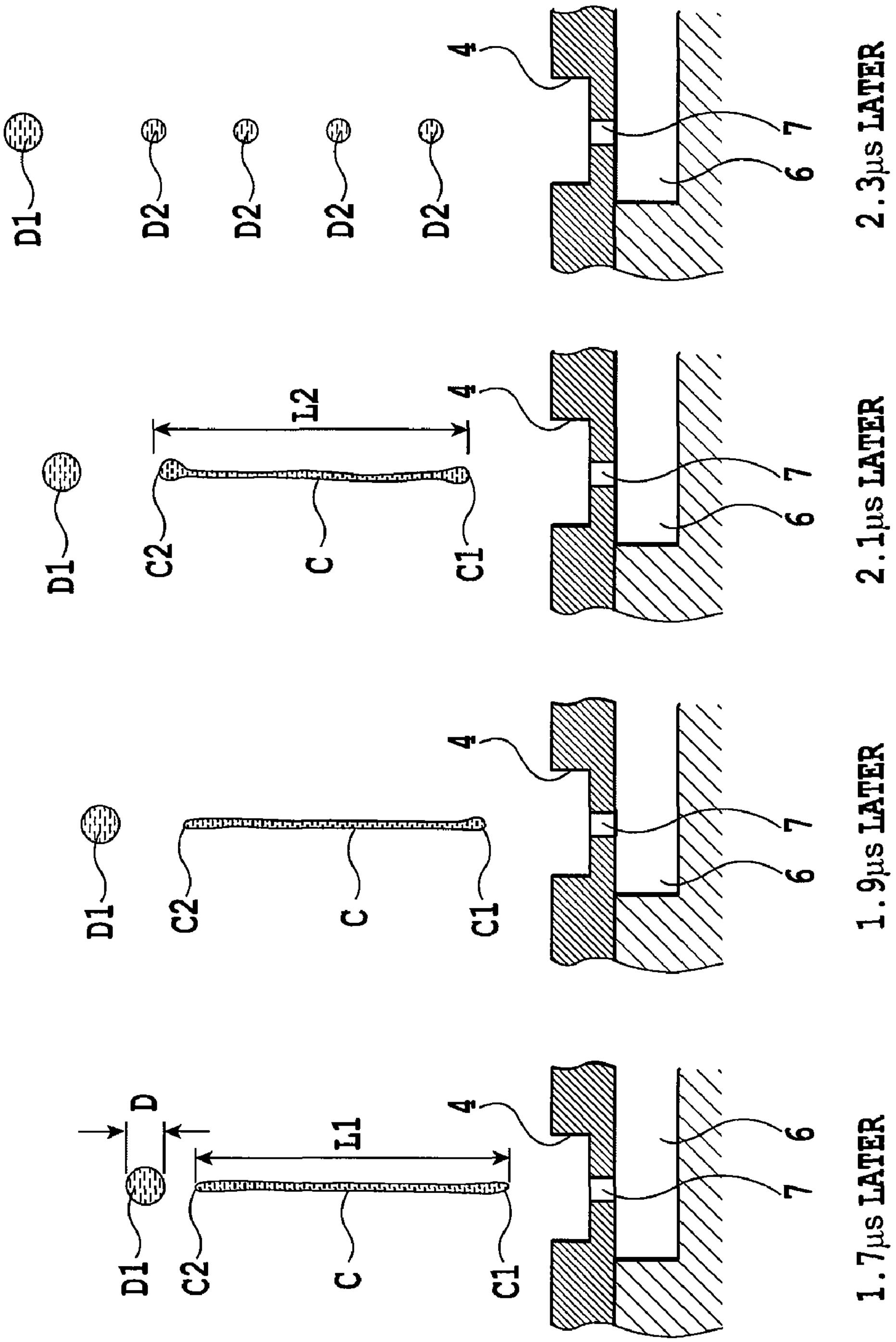
FIGS. 3A to 3D are diagrams illustrating a process in which the liquid ejection head in FIG. 1 forms droplets.

When the liquid ejection head configured as described above was used to eject the chemical, a main droplet D1 with a diameter D of 3 μm and succeeding four satellites (sub-droplets) D2 of diameter about 1 to 2 μm were generated as shown in FIG. 3D. In FIGS. 3A to 3D, the surface shape of the chemical in the ejection port 4 and the shape of a bubble in the chemical channel are not shown. The voltage of a driving pulse to be applied to the heater 1 was 1.5 times (this value is the same as that in Comparative Example 3, described below) as high as that in Comparative Example 1, described below, that is, 12.7 V. The width (pulse width) of the driving pulse in the present embodiment was set to 1.2 μs. The ejected liquid had a viscosity of 1 cP and a surface tension of 30 dyn/cm.

In the field of ink jet printing, the diameter of the main droplet is generally larger than 10 μm (volume: 0.5 picoliters). The diameter of the satellite is rarely equivalent to that of the main droplet. Thus, in the field of ink jet printing, no attempt has been made to reduce the difference in diameter between the satellite and the main droplet to between 1 μm and 2 μm as is the case with the present invention.

The sizes of the five droplets, that is, the one main droplet D1 and the four satellites D2, are all effective for treatment in the field of drug suction. A single application of a driving pulse allowed as many as five such chemical droplets to be efficiently generated. Compared to Comparative Example 1, described below, the present embodiment slightly reduced the diameters of the droplets but increased the number of ejected droplets by 2.5-fold. Thus, the energy required to eject the chemical was successfully saved. In the field of drug suction, several tens of microlitters of drug need to be nebulized every second in the form of small droplets of diameter about 3 μm (volume: 0.014 picolitters). In the liquid ejection head ejecting the liquid using the heaters 1 as in the case of the present example, the liquid ejection condition tends to be varied by a rise in temperature of the liquid ejection head caused by heat from the heaters 1. However, in the present example, the energy required to eject the chemical can be saved, thus very effectively allowing a sufficient amount of drug to be nebulized with a possible rise in the temperature of the liquid ejection head prevented.

FIGS. 3A, 3B, 3C, and 3D are diagrams illustrating the chemical ejection condition observed 1.7 μs, 1.9 μs, 2.1 μs, and 2.3 μs after the application of the driving pulse.

The process in which the satellite D2 was generated was observed. First, as shown in FIG. 3A, a liquid column projecting from the liquid surface of the chemical in the ejection port 4 was separated into the main droplet D1 and the liquid column C. Even with a slight variation from one chemical ejection operation to another, the length of the liquid chemical C was at least eight times as large as the diameter D of the main droplet D1. The length L1 of the liquid column C in FIG. 3A was observed immediately after the liquid column C was separated from the liquid surface (the surface of the liquid) of the chemical in the ejection port 4 and from the main droplet D1. Thus, the liquid column C separated from the liquid surface of the chemical in the ejection port 4 and the main droplet D1 is also called a separated liquid column. Furthermore, the length L2 of the liquid column C in FIG. 3C was observed immediately before the liquid column C was separated into a plurality of the satellites D2 by surface tension. The lengths L1 and L2 met the following relation.

$$(L2/L1) \geqq 0.9$$

This means that during the period between FIG. 3A and FIG. 3D, there was almost no difference between the speed V1 of an end C1 of the liquid column C which was closer to the ejection port 4 and the speed V2 of the other end C2 of the liquid column C. The length of the liquid column C varies slightly from one ejection operation to another. Thus, the length was evaluated based on truncation to two decimal places. Around a point in time when a constricted part is formed between the liquid surface of the chemical in the liquid column C and the trailing end of the liquid column C, that is, around a point in time when the formation of the constricted part following the separation of the liquid column C from the liquid surface of the chemical in the ejection port 4, the speed of the leading end C2 of the liquid column C is desirably at least 20 m/s.

As described above, in the ejection head in the present example, the ejection port 4 was formed outside the pore 7 of diameter 2 μm and filled with the chemical. The ejection head further included the flow resistance member 9. Thus, the chemical in the ejection port 4 was continuously fed to a liquid column formed by the high-speed flow of the chemical flowing through the pore 7. As a result, the liquid column was formed to be long without being cut into short fractions. The flow resistance member 9 increases the flow resistance of the chemical flowing from the individual liquid chamber 6 toward the common liquid chamber 8, located behind the individual liquid chamber 8. As a result, during driving of the heater 1, the amount of the chemical flowing from the individual liquid chamber 6 toward the ejection port 4 is increased to form a "high-speed" flow. This allows the chemical to be efficiently ejected. During the actual detailed observation of formation of a liquid column, while the liquid column grew by projecting outward from the ejection port, a constricted part was formed in the liquid column (about 0.4 μs after the application of the driving pulse). The leading end of the liquid column exhibited a high average speed of at least 20 m/s around the point in time when the constricted part was formed.

Furthermore, during the formation of such an elongate liquid column, an unbalanced condition such that the thickness of the liquid column varies in the length direction as in the case of the comparative example described below does not continue. Thus, the liquid column moves in a direction of a balanced condition such that the liquid column maintains an almost uniform thickness in the length direction. This is expected to be because the liquid column is thinner than in the comparative example described below, so that the resulting surface tension relatively enhances the effect of uniformizing the thickness of the liquid column. This is the same as a phenomenon in which an increase in the diameter of a droplet with the same surface tension makes the droplet likely to be deformed by disturbance, whereas a reduction in diameter makes the droplet unlikely to be deformed, with the resultant diameter likely to be held.

As shown in FIG. 3A, external energy is no longer applied to the separated liquid column C separated from the liquid surface of the chemical in the ejection port 4 and from the main droplet D1. Thus, the separated liquid column is rounded at the opposite ends thereof. C1 and C2 by surface tension but maintains an almost uniform thickness in the other portions.

Such a balanced condition of the separated liquid column C prevents the flow of the chemical in the separated liquid column C. The difference in speed between the opposite ends C1 and C2 is also eliminated, with the length of the separated liquid column C almost unchanged. Since the separated liquid column was elongate compared to that in Comparative Example 1, described below, the droplet was split into a plurality of the satellites D2 in a short time of 0.5 μs before being shortened by the surface tension. Thus, the satellites D2, into which the droplet is split, stochastically have almost the same size. This is expected to be why the plurality of satellites D2 of an equal size (the difference in diameter was 1 to 2 μm) were successfully formed.

Furthermore, the process of growth of the separated liquid column separated from the liquid surface of the chemical in the ejection port 4 and from the main droplet D1 may be either (1) or (2). The separated liquid column is separated from the liquid surface of the chemical in the ejection port 4 while the chemical remains in the ejection port 4.

(1) The liquid column is separated from the liquid surface of the liquid in the ejection port 4 and then main droplet is separated from the liquid column to form the separated liquid column.

(2) The main droplet is separated from the leading end of the liquid column extending outward from the liquid surface of the chemical in the ejection port 4. Then, the liquid column is separated from the liquid surface of the liquid in the ejection port 4 to form the separated liquid column.

Such a separated liquid column was approximated by a cylinder with a diameter defined by d and a length defined by L1. The length L1 was examined which was obtained when "at least three satellites D2 of the same diameter as that of the main droplet D1 were formed from the separated liquid column".

$$\pi\cdot(d/2)^2\times L1 \geqq 3\times\{(4\pi/3)\times(D/2)^3\} \quad (1)$$

In Formula (1), the left side expresses the volume of the separated liquid column approximated by the cylinder. The right side expresses the volume of the three satellites. Formula (1) can be modified to Formula (2).

$$L1 \geqq 2\cdot(D/d)^2\times D \quad (2)$$

In Formula (2), if (D/d)=2, the length L1 of the separated liquid column is at least eight times as large as the diameter D of the main droplet D1. This approximately matches the observation results. That is, when the length and diameter of the separated liquid column C observed immediately after the formation as shown in FIG. 3A are defined as L1 and d, respectively, setting the ratio (L1/D) of the length L1 to the diameter D of the main droplet D1 to at least eight allows at least three satellites D2 to be formed. This approximately matches the observation results.

However, in the case of Embodiment 1, the size of the satellite D2, that is, the diameter thereof, is about 1 to 2 μm and is thus smaller than that of the main droplet D1, that is, 3 μm. Thus, the four satellites D2 were generated. To increase the number of satellites, the waveform of the driving pulse may be adjusted so as to increase the length Lx of the separated liquid column, or the shape of the individual liquid chamber 6, the size of the heater 1, the size, shape, or position of the flow resistance member 9, or the like may be appropriately adjusted.

If the intended use is the drug suction according to the present invention, the nebulized droplet preferably has a diameter of at most 10 μm (volume: at most 0.5 pl) so as to be efficiently absorbed into the body. To allow the droplets to be more reliably absorbed through the lungs, the droplets preferably have a diameter of at most 5 μm (volume: at most 0.065 pl). Furthermore, when too small droplets are nebulized, the nebulized droplets may float and fail to reach the target site. Thus, each of the droplets is preferably at least 1 μm in diameter (volume: at least 0.0005 pl). That is, the size of the droplet is preferably such that 1.0 μm≦diameter≦5.0 μm and 0.0005 pl≦volume≦0.065 pl.

Furthermore, a maximum number of droplets each with a size within the above-described range are preferably efficiently ejected during a single driving operation. That is, at least five droplets are preferably ejected from a single ejection port during a single driving operation. Moreover, the five ejected droplets are preferably such that 1.0 μm≦diameter≦5.0 μm and 0.0005 pl≦volume≦0.065 pl. Provided that at least five droplets each with a size within the above-described range are ejected, sub-droplets of diameter smaller than 1.0 μm may further be generated.

Second Embodiment

In a second embodiment, the voltage of a driving pulse applied to each heater 1 was set to be 1.5 times as high as that in the first embodiment. The other conditions are the same as those in the first embodiment.

As a result, a main droplet D1 of diameter 3 μm and succeeding six satellites D2 of diameter about 1 to 2 μm were generated. All of these seven droplets (D1 and D2) have sizes effective for treatment in the field of drug suction. Compared to Comparative Example 1, described below, the present embodiment increased the number of ejected droplets by 3.5-fold in spite of a slight increase in droplet diameter.

The process in which the satellite D2 was generated was observed. First, as is the case with the above-described embodiment, the liquid column projecting from the liquid surface of the chemical in an ejection port 4 was separated into the main droplet D1 and the liquid column C. Even with a slight variation from one chemical ejection operation to another, the length of the liquid column C was at least 12 times as large as the diameter D of the main droplet D1. As is the case with the above-described embodiment, the length of the liquid column C observed immediately after the liquid column C was separated from the liquid surface of the chemical in the ejection port 4 and from the main droplet D1 was defined as L1. The length of the liquid column C observed immediately before the liquid column C was separated into a plurality of the satellites D2 by surface tension was defined by L2. As is the case with the first embodiment, the lengths L1 and L2 met the following relation.

$$(L2/L1) \geqq 0.9$$

This means that during the period between the time when the length L1 was measured and the time when the length L2 was measured, there was almost no difference between the speed V1 of an end C1 of the liquid column C which was closer to the ejection port 4 and the speed V2 of the other end C2 of the liquid column C. The length of the liquid column C varies slightly from one ejection operation to another. Thus, the length was evaluated based on truncation to two decimal places.

In the present embodiment, as is the case with the first embodiment, the ejection head included the flow resistance member 9. Thus, the chemical in the ejection port 4 was continuously fed to the liquid column formed by the high-speed flow of the chemical flowing through the pore 7. As a result, the liquid column was formed to be long without being cut into short fractions. Furthermore, during the formation of such an elongate liquid column, an unbalanced condition such that the thickness of the liquid column varies in the length direction as in the case of the comparative example described below does not continue. Thus, the liquid column moves in a direction of a balanced condition such that the liquid column maintains an almost uniform thickness in the length direction. This is expected to be because the liquid column is thinner than in the comparative example described below, so that the resulting surface tension relatively enhances the effect of uniformizing the thickness of the liquid column. This is the same as a phenomenon in which an increase in the diameter of a droplet with the same surface tension makes the droplet likely to be deformed by disturbance, whereas a reduction in diameter makes the droplet unlikely to be deformed, with the resultant diameter likely to be held.

Thereafter, external energy is no longer applied to the separated liquid column C separated from the liquid surface of the chemical in the ejection port 4 and from the main droplet D1. Thus, the separated liquid column is rounded at the opposite ends thereof. C1 and C2 by surface tension but maintains an almost uniform thickness in the other portions. Such a balanced condition of the separated liquid column C prevents the flow of the chemical in the separated liquid column C. The difference in speed between the opposite ends C1 and C2 is also eliminated, with the length of the separated liquid column C almost unchanged. Since the separated liquid column was elongate compared to that in Comparative Example 1, described below, the droplet is split into a plurality of the satellites D2 before being shortened by the surface tension. Thus, the satellites D2, into which the droplet is split, stochastically have almost the same size. This is expected to be why the plurality of satellites D2 of an equal size (the difference in diameter was 1 to 2 μm) were successfully formed.

Third Embodiment

In a third embodiment, a liquid ejection head was produced with the diameter of each pore 7 set to 5 μm. The voltage of a driving pulse applied to each heater 1 was set to 13.5 V. The other conditions are the same as those in the first embodiment.

As a result, a main droplet D1 of diameter 7 μm and succeeding four satellites D2 of diameter about 1 to 4 μm were generated. All of these five droplets (D1 and D2) have sizes effective for treatment in the field of drug suction. Compared to Comparative Example 1, described below, the present embodiment increased the number of ejected droplets by 2.5-fold in spite of a slight increase in droplet diameter.

The process in which the satellite D2 was generated was observed. First, as is the case with the above-described embodiments, a liquid column projecting from the liquid surface of the chemical in an ejection port 4 was separated into the main droplet D1 and the liquid column C. Even with a slight variation from one chemical ejection operation to another, the length of the liquid column C was at least eight times as large as the diameter D of the main droplet D1. As is the case with the above-described embodiment, the length of the liquid column C observed immediately after the liquid column C was separated from the liquid surface of the chemical in the ejection port 4 and from the main droplet D1 was defined as L1. The length of the liquid column C observed immediately before the liquid column C was separated into a plurality of the satellites D2 by surface tension was defined as L2. As is the case with the first embodiment, the lengths L1 and L2 met the following relation.

$$(L2/L1) \geqq 0.9$$

This means that during the period between the time when the length L1 was measured and the time when the length L2 was measured, there was almost no difference between the speed V1 of an end C1 of the liquid column C which was closer to the ejection port 4 and the speed V2 of the other end C2 of the liquid column C. The length of the liquid column C varies slightly from one ejection operation to another. Thus, the length was evaluated based on truncation to two decimal places.

In the present embodiment, as is the case with the first embodiment, the ejection head included the flow resistance member 9. Thus, the chemical in the ejection port 4 was continuously fed to the liquid column formed by the high-speed flow of the chemical flowing through the pore 7. As a result, the liquid column was formed to be long without being cut into short fractions.

Thereafter, external energy is no longer applied to the separated liquid column C separated from the liquid surface of the chemical in the ejection port 4 and from the main droplet D1. Thus, the separated liquid column is rounded at the opposite ends thereof. C1 and C2 by surface tension but maintains an almost uniform thickness in the other portions. Such a balanced condition of the separated liquid column C prevents the flow of the chemical in the separated liquid column C. The difference in speed between the opposite ends C1 and C2 is also eliminated, with the length of the separated liquid column C almost unchanged. Since the separated liquid column C was elongate compared to that in Comparative Example 1, described below, the droplet is split into a plurality of the satellites D2 before being shortened by the surface tension. Thus, the satellites D2, into which the droplet is split, stochastically have almost the same size. This is expected to be why the plurality of satellites D2 of an equal size were successfully formed.

Comparative Example 1

Figure 6:
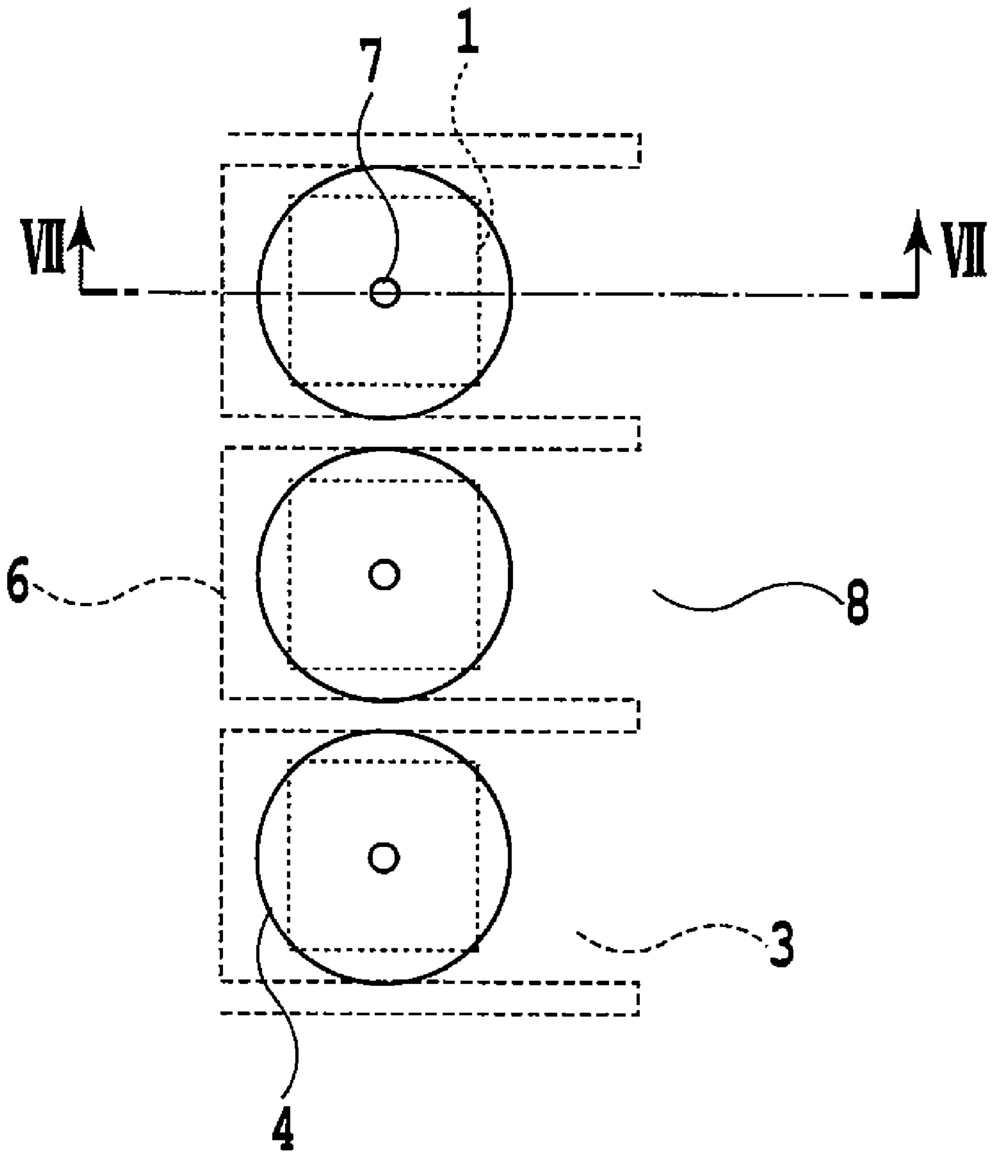
FIG. 6 is a plan view of an essential part of a liquid ejection head in a comparative example.
Figure 7:
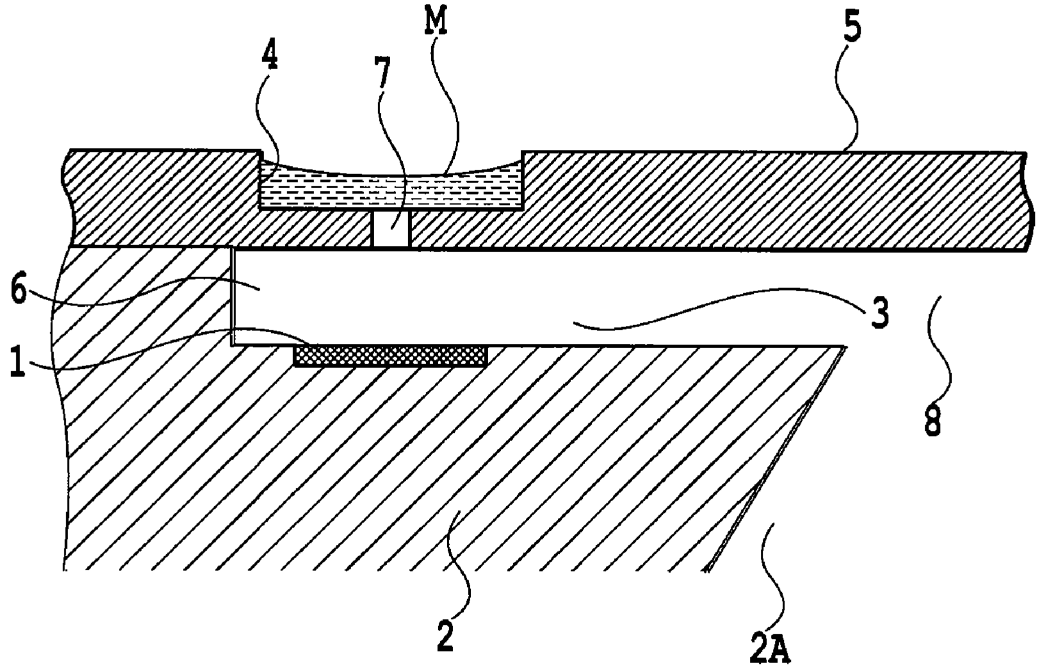
FIG. 7 is a sectional view taken along line VII-VII in FIG. 6.

A liquid ejection head in Comparative Example 1 did not include the flow resistance member 9 according to the first embodiment of the present invention. The diameter of pores 7 was set to 3 μm. FIG. 6 is a plan view of an essential part of the liquid ejection head in Comparative Example 1. FIG. 7 is a sectional view taken along line VII-VII in FIG. 6. The voltage of a driving pulse for the liquid ejection head produced as described above was set to 12.7 V. The other conditions are the same as those in the first embodiment of the present invention described above.

Figures 8A, 8B, 8C, 8D:
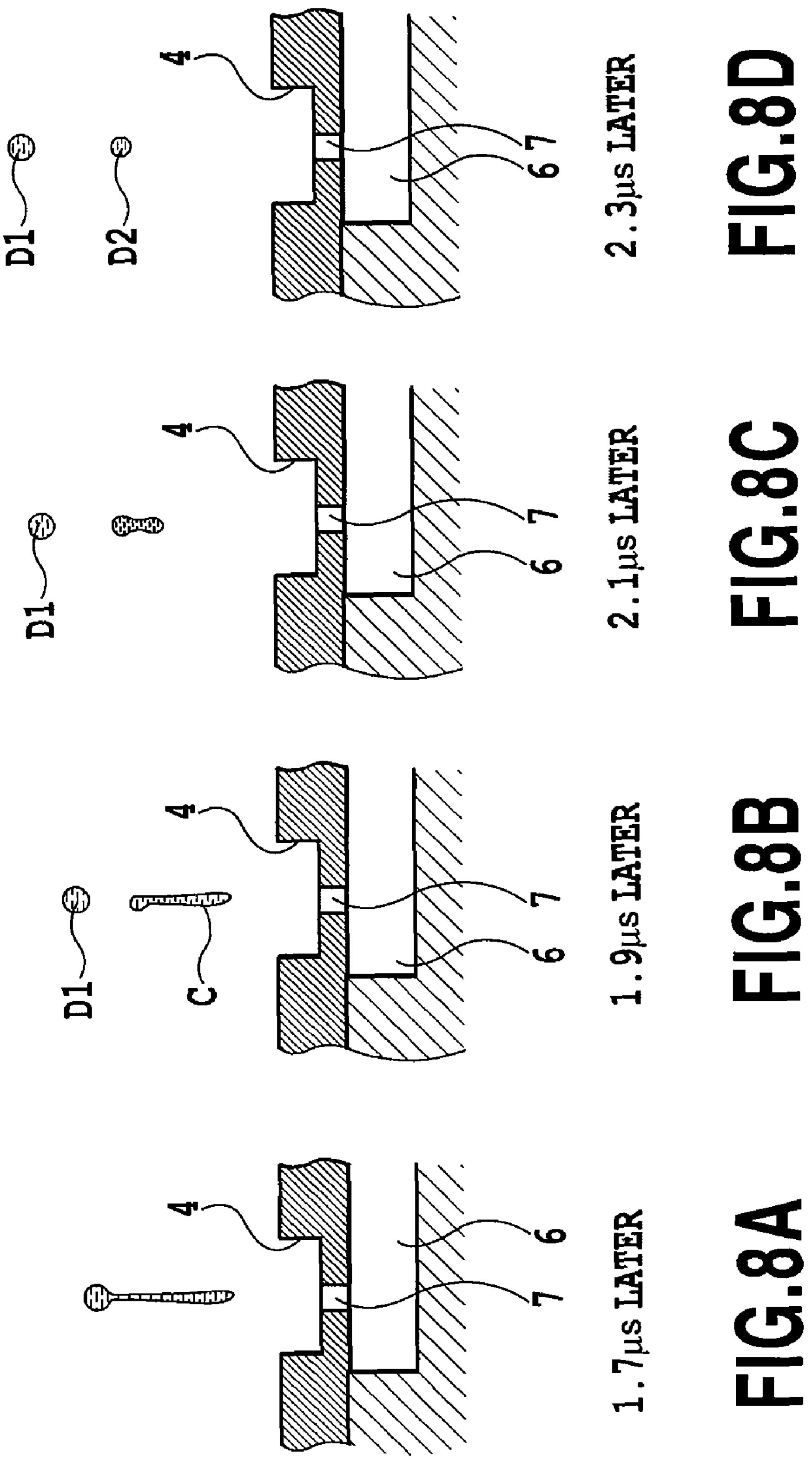
FIGS. 8A to 8D are diagrams illustrating a process in which the liquid ejection head in FIG. 6 forms droplets.

When the chemical was ejected by the liquid ejection head in Comparative Example 1, a main droplet D1 of diameter 4 μm and one satellite (sub-droplet) of diameter 3 μm were generated as shown in FIG. 8D. In FIGS. 8A to 8D, as in the case of FIG. 3, described above, the shape of the liquid surface of the chemical in an ejection port 4 and the shape of a bubble in a chemical channel are not shown.

The process in which the satellite D2 was generated was observed. First, as shown in FIGS. 8A and 8B, a liquid column projecting from the liquid surface of the chemical in the ejection port 4 to the exterior was separated into a main droplet and a liquid column. Immediately after being separated from the liquid surface of the chemical in the ejection port 4 and from the main droplet D1, the separated liquid column C had a short length about three times as large as the diameter of the main droplet D1. Thereafter, the opposite ends of the separated liquid column started to be rounded by surface tension. Then, 0.6 μs later, the initially short separated liquid column was rapidly shortened into one droplet (satellite).

In Comparative Example 1, the difference in diameter between the satellite and the main droplet was 1 μm. Thus, the satellite and the main droplet were almost the same in size. Furthermore, although only one satellite was generated, the sizes of the main droplet of diameter 4 μm and the satellite of diameter 3 μm are both effective for treatment in the field of drug suction.

Comparative Example 2

In Comparative Example 2, the diameter of pores 7 was set to 2 μm. The other conditions are the same as those in Comparative Example 1.

However, in Comparative Example 2, the liquid surface of the chemical in the ejection port 4 rose, but the chemical failed to be ejected. This is expected to be because the diameter of the pores 7 set to a small value of 2 μm increased the flow resistance of the chemical.

Comparative Example 3

A driving pulse with a voltage 1.5 times as high as 12.7 V was applied to the liquid ejection head in Comparative Example 2. However, the chemical still failed to be ejected. This is expected to be because the diameter of the pores 7 set to a small value of 2 μm increased the flow resistance of the chemical.

Comparative Example 4

A driving pulse with a width that is twice 1.2 μs (=(1.2×2 (μs)) was applied to the liquid ejection head in Comparative Example 2. However, the chemical still failed to be ejected. This is expected to be because the diameter of the pores 7 set to a small value of 2 μm increased the flow resistance of the chemical.

Comparative Example 5

A driving pulse with a width that was twice 1.2 μs (=(1.2×2 (μs)) was applied to the liquid ejection head in Comparative Example 3. However, the chemical still failed to be ejected. This is expected to be because the diameter of the pores 7 set to a small value of 2 μm increased the flow resistance of the chemical.

The results of examinations of Comparative Examples 1 to 5 indicate that when the diameter of the pores 7 is set to a small value of 2 μm, the resultant increased flow resistance of the chemical prevents the chemical from being ejected in spite of an increase in the voltage or pulse width of the driving pulse. The increased flow resistance of the chemical in the pore 7 prevents a bubble generated in the individual liquid chamber 6 from efficiently forming the flow of the chemical toward the pore 7. The bubble grows significantly only toward the common liquid chamber 8.

Other Embodiments

In the above-described embodiment, the heaters (electrothermal transducing elements) capable of bubbling the liquid are used as energy generation portions generating energy required to eject the liquid. However, the energy generation portions are not limited to the heaters, but piezo elements or the like may be used. A liquid ejection scheme using the piezo elements or the like allows a large number of droplets to be efficiently generated by a single operation of driving the energy generation portions (a single application of a driving pulse).

A plurality of pores 7 may be formed which are connected to the individual liquid chamber 6. This enables a further increase in the number of droplets that can be generated by a single input of a driving pulse.

The shape of the flow resistance member 9 is not limited to the cylinder but may be appropriately changed. The number of flow resistance member 9 formed in the liquid channel is not limited to one as is the case with the above-described embodiment. A plurality of flow resistance members 9 may be formed.

The liquid ejection head applied to the drug suction apparatus may be coupled to a drug dispenser. The drug to be ejected may be a protein formulation such as insulin, human-growth hormone, or gonadotropic hormone, or nicotine or an anesthetic.

The present invention allows the effective use of a liquid ejection head that enables a liquid in individual liquid chambers to be ejected from respective ejection ports through corresponding throttling portions. Furthermore, the present invention has only to allow the energy generation portion to be driven so as to set the relationship $(L2/L1) \geqq 0.9$ for the length L1 of the liquid column observed immediately after the liquid column has been separated from the main droplet and from the liquid in the ejection port and the length L2 thereof observed immediately before the liquid column is separated into a plurality of sub-droplets. Additionally, a larger number of droplets can be formed by setting the ratio (L1/D) of the length L1 to the diameter D of the main droplet to at least 8 so that while the liquid remains in the ejection port, the liquid column is separated from the liquid surface in the ejection port. Moreover, a large number of droplets can be reliably and stably formed by setting the speed of the leading end of the liquid column projecting outward from the liquid surface of the liquid in the ejection port so that the speed is at least 20 m/s around a point in time when a constricted part is formed in the liquid column.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-142678, filed May 30, 2008, which is hereby incorporated by reference herein in its entirety.

What is claimed is:

1. A liquid ejection method of ejecting a liquid containing a drug to be sucked into lungs, the method comprising the steps of:

preparing a liquid ejection head having an individual liquid chamber including an energy generation portion generating energy required to eject the liquid, an ejection port formed of a recess portion to internally hold the liquid, and a throttling portion formed to have a smaller opening than the ejection port and allowing the individual liquid chamber and the ejection port to communicate with each other, an open end on the ejection port side of the throttling portion being covered by liquid held in the recess portion; and driving the energy generation portion so as to eject a main droplet and a liquid column from the ejection port, the liquid column to be separated into a plurality of sub-droplets, wherein a relationship $(L2/L1) \geqq 0.9$ is set for length L1 of the liquid column observed immediately after the liquid column has been separated from the main droplet and from the liquid in the ejection port and length L2 of the liquid column observed immediately before the liquid column is separated into the plurality of sub-droplets.

2. The liquid ejection method according to claim 1, wherein a ratio (L1/D) of the length L1 to diameter D of the main droplet is at least 8, and while the liquid remains in the ejection port, the liquid column is separated from a liquid surface in the ejection port.

3. The liquid ejection method according to claim 1, wherein the diameter of the main droplet is at most 10 μm.

4. The liquid ejection method according to claim 1, wherein speed of a leading end of the liquid column projecting outward from the liquid surface of the liquid in the ejection port is set to be at least 20 m/s around a point in time when a constricted part is formed in the liquid column.

5. A liquid ejection method of ejecting a liquid containing a drug to be sucked into lungs, the method comprising the steps of:

preparing a liquid ejection head having an individual liquid chamber including an energy generation portion generating energy required to eject the liquid, an ejection port formed of a recess portion to internally hold the liquid, and a throttling portion formed to have a smaller opening than the ejection port and allowing the individual liquid chamber and the ejection port to communicate with each other, an open end on the ejection port side of the throttling portion being covered by liquid held in the recess portion; and driving the energy generation portion so as to eject a main droplet and a liquid column from the ejection port, the liquid column being to be separated into a plurality of sub-droplets, wherein droplets ejected from one ejection port by a single operation of driving the energy generation portion and containing the main droplet and the sub-droplets contains at least five droplets each of diameter at least 1.0 μm and at most 5.0 μm.

* * * * *